United States Patent [19]

Kaufhold et al.

[11] Patent Number: 4,506,102

[45] Date of Patent: Mar. 19, 1985

[54] 2-METHOXYETHYL CYCLODODECENYL ETHER AND PROCESSES FOR ITS PREPARATION AND CONVERSION TO 2-METHOXYETHYL CYCLODODECYL ETHER

[75] Inventors: Manfred Kaufhold, Marl, Fed. Rep. of Germany; Hendrik J. Takken, HN Huizen, Netherlands

[73] Assignees: Chemische Werke Huls AG, Marl, Fed. Rep. of Germany; Naarden International N.V., Naarden, Netherlands

[21] Appl. No.: 498,628

[22] Filed: May 27, 1983

[30] Foreign Application Priority Data

May 27, 1982 [DE] Fed. Rep. of Germany ....... 3219915

[51] Int. Cl.³ .................... C07C 41/01; C07C 43/184; C07C 43/188
[52] U.S. Cl. ..................................... 568/667; 568/670
[58] Field of Search ........................ 568/667, 591, 670

[56] References Cited

U.S. PATENT DOCUMENTS 3,875,241  4/1975  Corbier et al. ...................... 568/667
3,903,006  9/1975  Elliott et al. ........................... 252/79
4,317,942  3/1982  Burzin ................................. 568/670

OTHER PUBLICATIONS

Ellis, Hydrogenation of Organic Substances (1930) [item 2138] 234.
Houben-Weyl, "Methoden der Organischen Chemie", GTV 1965, 11–19, 24–29, 32–34.

Primary Examiner—Bernard Helfin
Attorney, Agent, or Firm—Millen & White

[57] ABSTRACT

2-Methoxyethyl cyclododec-1-enyl ether is of interest as a precursor for the saturated ether, 2-methoxyethyl cyclododecyl ether, which can be obtained therefrom by catalytic hydrogenation, in a high purity and with a good fragrance quality. The saturated ether is a valuable fragrance component having a woody note. A process for producing 2-methylethyl cyclododec-1-enyl ether comprises the step of reacting cyclododecanone, 2-methoxyethanol and a tri(lower alkyl) orthoformate, at a temperature of 50°–250° C., in the presence of an acid catalyst, removing resultant low-boiling compounds by distillation, and recovering resultant 2-methoxyethyl cyclododec-1-enyl ether.

18 Claims, No Drawings

2-METHOXYETHYL CYCLODODECENYL ETHER AND PROCESSES FOR ITS PREPARATION AND CONVERSION TO 2-METHOXYETHYL CYCLODODECYL ETHER

BACKGROUND OF THE INVENTION

This invention relates to 2-methoxyethyl cyclododec-1-enyl ether, as well as a process for its preparation from cyclododecanone and for its conversion to the valuable fragrance component, 2-methoxyethyl cyclododecyl ether.

The 2-methoxyethyl cyclododec-1-enyl ether of Formula I

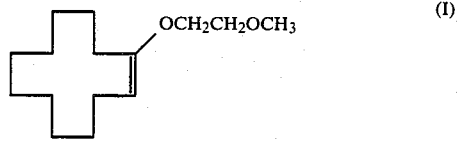

is of great interest as a suitable precursor for 2-methoxyethyl cyclododecyl ether of Formula II

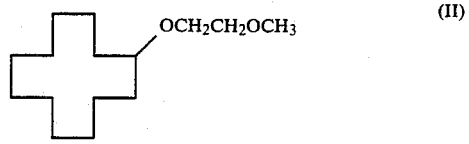

The corresponding saturated ether can be produced in high purity and with good fragrance quality by the catalytic hydrogenation of (I). 2-Methoxyethyl cyclododecyl ether (II) is a valuable component in the manufacture of odoriferous substance compositions for perfume or, inter alia, for the perfuming of cosmetics, as disclosed in, e.g., DOS No. 2,928,348, corresponding to U.S. Pat. No. 4,317,942.

Heretofore, 2-methoxyethyl cyclododecyl ether could be prepared only with the aid of expensive, multistage processes by way of the 2-hydroxyethyl cyclododecyl ether of Formula III

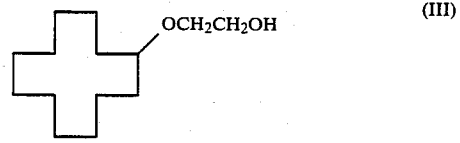

While (III) per se can be prepared relatively easily, for example, by hydrogenation of the ketal formed from cyclododecanone and ethylene glycol, the etherification of this alcohol can be achieved only with great technical expenditure, since the alcohol employed is not completely reacted in the conventional etherification processes, as disclosed, e.g., in Houben-Weyl, "Methoden der organischen Chemie" Vol. VI/3, "Sauerstoffverbindungen" I, part 3, pp. 10–137 (1965). The residual alcohol in the ether, however, precludes the use of the latter as a fragrance component, due to the unpleasant odor of the alcohol. Separation of these products by distillation is not very effective due to their very similar boiling points. The extraction and absorption methods proposed in DOS No. 2,928,348 likewise are only successful with very great technical expenditure. Chemical methods are also unsuitable, for economic reasons.

Furthermore, according to the examples in DOS No. 2,928,348, expensive chemicals are required for etherification, such as, e.g., sodium amide and dimethyl sulfate, whose handling is also hazardous. These are modes of operation which, though feasible on a laboratory scale, cannot be considered for industrial realization because of the high costs for starting materials and the great technical expense required to ensure the safety of personnel.

Consequently, all of the conventional processes yield only an impure product, require expensive technical apparatus, or employ chemicals which are expensive and, due to handling problems, suitable only for laboratory work.

OBJECTS OF THE INVENTION

One object of the present invention is to provide a process for producing 2-methoxyethyl cyclododecyl ether in a simple way with low technical expenditure, in high purity and in good yield.

Another object of the invention is to provide a stable, readily isolable intermediate which is easily converted to the saturated ether (II).

SUMMARY OF THE INVENTION

These objectives have been attained according to this invention by providing a process for preparing the novel intermediate, 2-methoxyethyl cyclododec-1-enyl ether, comprising the step of reacting cyclododecanone, 2-methoxyethanol and a tri(lower alkyl)orthoformate, at a temperature of 50°–250° C., in the presence of an acid catalyst, removing resultant low-boiling compounds by distillation, and recovering resultant 2-methoxyethyl cyclododec-1-enyl ether. Catalytic hydrogenation of this ether (I) produces the saturated ether (II).

DETAILED DISCUSSION

It is possible, surprisingly, to obtain 2-methoxyethyl cyclododecenyl ether (I) in high yields of above 93% and with a purity of above 99%, in a single stage, by reaction of cyclododecanone with a tri(lower alkyl)orthoformate, i.e., an orthoformic acid ester of a $C_{1-4}$-alkanol, and with 2-methoxyethanol, in the presence of an acid catalyst.

The synthesis can also be effected in two stages, instead of in one stage. By first producing the orthoformic acid ester of 2-methoxyethanol in accordance with the disclosure of DAS No. 2,062,034, corresponding to U.S. Pat. No. 3,903,006, only low yields are obtained in the second stage reaction with cyclododecanone. In contrast thereto, by first reacting cyclododecanone with a tri(lower alkyl)orthoformate, in the presence of a $C_{1-4}$-alkanol as the solvent, and then reacting the reaction mixture obtained in the first stage with 2-methoxyethanol in a second stage, increased yields are obtained, but the conversion is unsatifactory.

In principle, when the reaction is carried out in one stage (one-pot process) there are substantially more possibilities for secondary reactions. Surprisingly and unexpectedly, however, considerably higher yields can be obtained, with conversions of 98% and higher, as well as a purer product. Since 2-methoxyethyl cyclododecenyl ether is a precursor for a fragrance compound, purity is a decisive criterion. For this reason, the present process is preferably carried out in a single stage.

An additional advantage of the process of this invention is that the novel enol ether (I) is obtained by a simple process, this compound being relatively stable and lending itself readily to purification by means of distillation.

The process of this invention, for economic reasons, is preferably conducted under atmospheric pressure, the maximum reaction temperature in this case being the boiling point of the reaction mixture. Thus, after combining the components, resultant low-boiling compounds are immediately removed by distillation, under agitation. In this process, the reaction temperature is increased from 50° to 250° C., preferably from 70° to 190° C., especially from 70° to 160° C., so that distillate is continuously obtained. Temperatures of above 250° C. are unsuitable since strong decomposition of the formic acid esters occurs in such a case. Preferably, the reaction is conducted in an inert gas atmosphere, e.g., under nitrogen.

Once no more distillate is obtained, even when the reaction temperature is raised to 250° C., or 190°, or 160° C., the pressure is reduced to 10–25 mbar and, under this pressure, and at a temperature of up to 190° C., preferably up to 160° C., distillation is continued. After distillation of the residual low-boiling compounds is finished, the catalyst is neutralized, suitably, e.g., with 50% sodium hydroxide solution, and thereafter the unsaturated ether (I) is distilled, e.g., at 153°–163° C. and 13 mbar.

The process can be carried out in a batchwise or continuous fashion.

Esters of alcohols having a lower boiling point than 2-methoxyethanol, i.e., below 124° C., are suitable for use as the orthoformate esters (IV) in the process of this invention:

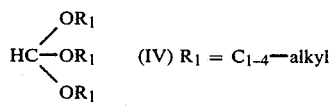

(IV) $R_1 = C_{1-4}$—alkyl

Preferably, commercially available trimethyl and triethyl orthoformates are utilized, of which the trimethyl ester produces the best yields.

Suitable acid catalysts include mineral acids, e.g., hydrogen chloride, sulfuric acid, and phosphoric acid, as well as typical Friedel-Crafts catalysts, e.g., chlorides of iron, zinc, tin, and aluminum. The best yield and the highest purity for (I) is obtained by using alkylbenzenesulfonic acids, such as, e.g., p-toluenesulfonic acid and $C_{10-13}$-alkylbenzenesulfonic acid. Use of the last-mentioned acid as catalyst results in a particularly low sulfur content of the unsaturated ether (I). This is important for the lifetime of the hydrogenation catalyst. The $C_{10}$-$C_{13}$-Alkylenebenzenesulfonic acid is commercially avalable (MARLON AS 3-Säure).

The acid catalyst is employed in amounts of from 0.2 to 1 g, preferably from 0.3 to 0.5 g, especially about 0.35 g, based on 100 g of ketone employed. The molar ratio of cyclododecanone to methoxyethanol is preferably between 1:1 and 1:5, more preferably between 1:2,5 and 1:3,5. The molar ratio of cyclododecanone to orthoformate is preferably between 1:1 and 1:3, more preferably between 1:1 and 1:1,5.

Suitable solvents are $C_{1-4}$-alkanols. They are required only for the two-stage method.

The resultant 2-methoxyethyl cyclododecenyl ether is a colorless to slightly yellowish, oily liquid having a characteristic "green" odor reminiscent of fresh grass; at 13 mbar, this compound has a relatively wide boiling range from about 153° to 163° C., because it is present as a mixture of two isomers. According to analysis by gas chromatography, the distillate contains two components in concentrations of, for example, 20.0% and 79.8%. These isomers are the cis and trans geometric isomers. They may be separated by, e.g., high performance gas chromatography. As used herein, 2-methoxyethylcyclododec-1-enyl ether includes the pure cis and/or the pure trans isomer or a mixture thereof.

2-Methoxyethyl cyclododecenyl ether is a particularly useful intermediate for the manufacture of 2-methoxyethyl cyclododecyl ether (II), a valuable odoriferous compound. Hydrogenation of (I) can be effected conventionally by contacting the unsaturated enol ether (I) with hydrogen gas, in the presence of a hydrogenation catalyst, e.g., at a hydrogen pressure of 15–300 bar, with a palladium or nickel catalyst, at an elevated temperature, e.g., 50°–100° C. The saturated 2-methoxyethyl cyclododecyl ether (II) is obtained with a purity of above 99% and good fragrance quality, i.e., absence of impurities having undesirable fragrance characteristics, e.g., sulfur-containing and/or chlorine-containing impurities, or reactants and/or reaction intermediates.

2-Methoxyethyl cyclododecyl ether (II) is useful for the manufacture of fragrance compositions, especially compositions having a typically woody fragrance note.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A glass apparatus is employed, consisting of a three-necked flask equipped with an agitator, a thermometer, and a distillation column with distilling head, variable reflux control, condenser, multiple fraction receiver, vacuum adapter, etc.

The starting material consists of 541.4 g (5 mol) of trimethyl orthoformate (98%), 1,141.5 g (15 mol) of 2-methoxyethanol, 911.5 g (5 mol) of cyclododecanone, and 3.1 g of $C_{10-13}$-n-alkylbenzenesulfonic acid, and the mixture is heated with agitation, under nitrogen, to boiling with refluxing. The low-boiling components produced during the reaction are removed by distillation, first at atmospheric pressure, and then at 16 mbar, as indicated in Table I.

Once the formation of distillate ceases at atmospheric pressure, at fraction 3, the pressure is reduced to 16 mbar, the temperature in the sump is again raised to 160° C., and the residual 2-methoxyethanol is removed by distillation. The mixture is then cooled and 5 ml of 50% sodium hydroxide solution is added to neutralize the catalyst. After this addition 0.5 g of soda is introduced and the reaction product is subjected to fractional distillation without any further work-up. Within a boiling range of 153°–163° C. at 13 mbar, 1,121 g of 2-methoxyethyl cyclododec-1-enyl ether is obtained with a purity of 99.8% as determined by gas chromatography. The yield, based on the starting material, is 93.2% of theory. The chlorine and sulfur contents are each about 1 ppm maximum.

2-Methoxyethyl cyclododecenyl ether is a colorless to slightly yellowish, oily liquid with a "green" fragrance reminiscent of fresh grass. According to analysis by gas chromatography, two isomers are present in concentrations of 20.0% and 79.8%; their boiling points are 310° and 324° C., respectively, as calculated from the chromatogram.

The proton NMR spectrum reveals characteristic proton resonance peaks as shown in Table II.

EXAMPLE 2

The reaction is conducted analogously to the procedure of Example 1, but in the presence of 6.5 g of p-toluene sulfonic acid in place of 3.1 g of $C_{10-13}$-n-alkyl-benzenesulfonic acid. The 2-methoxyethyl cyclododecenyl ether is obtained in the same yield, but with a sulfur content of 8 ppm. The chlorine content is 1 ppm maximum. This higher sulfur content can be lowered to <1 ppm S in the usual way, for example with the aid of a nickel catalyst.

TABLE I

| Fraction No. | Pressure mbar | Boiling Ranges in °C. Sump | Boiling Ranges in °C. Head | Amount g | Proportion Reflux to Product Removed | Product |
|---|---|---|---|---|---|---|
| 1 | 1,013 | 70–96 | 32–48 | 296 | 10:1 | Methyl formate |
| 2 | 1,013 | 98–128 | 62–64 | 309 | 5:1 | Methanol |
| 3 | 1,013 | 132–160 | 119–122 | 777 | 5:1 | 2-Methoxy-ethanol |
|   | 16 | 150–160 | 38 | | | |

TABLE II

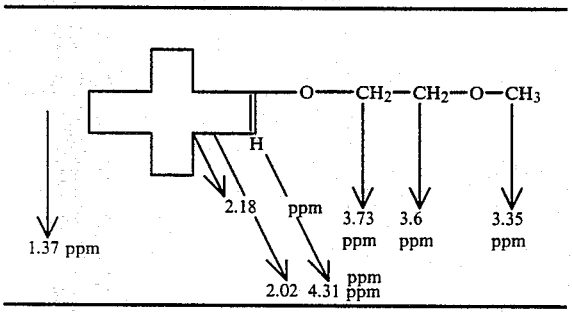

EXAMPLE 3

The reaction is conducted in the apparatus indicated in Example 1.

The starting materials are 364.6 g (2 mol) of cyclododecanone, 212.2 g (2 mol) of trimethyl orthoformate, 64.1 g (2 mol) of methanol, and 1.1 g of $C_{10-13}$-alkyl-benzenesulfonic acid.

This mixture is heated under agitation to above 70° C. until a distillate is obtained. The thus-formed methyl formate is removed by distillation as set forth in Example 1 until the boiling temperature of methanol has been reached. The mixture is then cooled in order to conduct the second step of the synthesis.

At this point in time, 456.6 g (6 mol) of 2-methoxyethanol is added, the mixture is again heated to boiling under agitation, and the low-boiling components, initially methanol, are removed by distillation. The process is further conducted as described in Example 1.

Yield: 70.5% Purity: 99.2%

EXAMPLE 4

In a 100-ml reactor, 2-methoxyethyl cyclododecenyl ether is conventionally hydrogenated with a feed of 20 ml per hour under a hydrogen pressure of 300 bar and at 50° C. over a supported palladium catalyst, thus obtaining 2-methoxyethyl cyclododecyl ether (II) in a practically quantitative yield and with a purity of above 98.5% as determined by gas chromatography. By distillation, the 2-methoxyethyl cyclododecyl ether is obtained in a yield of above 95% with good fragrance quality.

Practically the same results are obtained by lowering the pressure during hydrogenation from 300 bar to 15 bar and raising the temperature from 50° to 80° C.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:

1. 2-Methoxyethyl cyclododec-1-enyl ether.

2. The ether of claim 1, in a purity of higher than 99%.

3. The ether of claim 1, having sulfur and chlorine contents each of not more than about 1 ppm.

4. The ether of claim 1, in a purity of higher than 99%; and having sulfur and chlorine contents each of not more than about 1 ppm.

5. A process for preparing 2-methoxyethyl cyclododec-1-enyl ether, comprising the step of reacting cyclododecanone, 2-methoxyethanol and a tri(lower alkyl)orthoformate, at a temperature of 50°–250° C., in the presence of an acid catalyst, removing resultant low-boiling compounds by distillation, and recovering resultant 2-methoxyethyl cyclododec-1-enyl ether.

6. A process according to claim 5, wherein said acid catalyst is an alkylbenzenesulfonic acid.

7. A process according to claim 6, wherein said alkylbenzenesulfonic acid is toluenesulfonic acid or $C_{10-13}$-alkylbenzenesulfonic acid.

8. A process according to claim 5, wherein said reaction temperature is 70°–190° C.

9. A process according to claim 8, wherein said temperature is 70°–160° C.

10. A process according to claim 5, wherein said resultant low-boiling compounds are first removed by distillation at atmospheric pressure and then by distillation at a reduced pressure of 10–25 mbar at a temperature of up to 190° C.

11. A process according to claim 10, wherein said reduced pressure distillation is effected at a temperature of up to 160° C.

12. A process according to claim 5, wherein said orthoformate is trimethyl or triethyl orthoformate.

13. A process according to claim 5, wherein said reaction is effected in an inert gas atmosphere.

14. A process according to claim 5, wherein said resultant 2-methoxyethyl cyclododec-1-enyl ether has a purity of higher than 99%, and sulfur and chlorine contents each of not more than about 1 ppm.

15. A process for preparing 2-methoxyethyl cyclododecyl ether, comprising the steps of: (a) reacting cyclododecanone, 2-methoxyethanol and a tri(lower alkyl)orthoformate, at a temperature of 50°-250° C., in the presence of an acid catalyst, removing resultant low-boiling compounds by distillation, and recovering resultant 2-methoxyethyl cyclododec-1-enyl ether; and (b) contacting said resultant 2-methoxyethyl cyclododec-1-enyl ether with hydrogen in the presence of a hydrogenation catalyst, and recovering resultant 2-methoxyethyl cyclododecyl ether.

16. A process according to claim 15, wherein said catalyst is a palladium or nickel catalyst, and said hydrogenation is effected at a hydrogen pressure of 15-300 bar, and a temperature of 50°-100° C.

17. A process according to claim 15, wherein said 2-methoxyethyl cyclododecyl ether has a purity of higher than 99%.

18. A process according to claim 17, wherein said 2-methoxyethyl cyclododec-1-enyl ether has a purity of higher than 99%.

* * * * *